United States Patent
Soloveichik

(10) Patent No.: US 6,903,049 B2
(45) Date of Patent: Jun. 7, 2005

(54) METHOD AND CATALYST COMPOSITION FOR PRODUCING AROMATIC CARBONATES USING ACTIVATING SOLVENTS

(75) Inventor: Grigorii Lev Soloveichik, Latham, NY (US)

(73) Assignee: General Electric Company, Niskayuna, NY (US)

( * ) Notice: Subject to any disclaimer, the term of this patent is extended or adjusted under 35 U.S.C. 154(b) by 426 days.

(21) Appl. No.: 09/683,865

(22) Filed: Feb. 25, 2002

(65) Prior Publication Data

US 2003/0162652 A1 Aug. 28, 2003

(51) Int. Cl.⁷ .............................................. B01J 23/42
(52) U.S. Cl. ...................... 502/325; 502/326; 502/349; 502/350
(58) Field of Search ................. 502/164, 304, 502/324, 325, 326, 349, 350; 50/349

(56) References Cited

U.S. PATENT DOCUMENTS

| | | |
|---|---|---|
| 4,187,242 A | 2/1980 | Chalk |
| 5,132,447 A | 7/1992 | King, Jr. |
| 5,142,087 A | 8/1992 | Joerg et al. |
| 5,210,269 A | 5/1993 | Di Muzio et al. |
| 5,231,210 A | 7/1993 | Joyce et al. |
| 5,239,106 A | 8/1993 | Shafer |
| 5,284,964 A | 2/1994 | Pressman et al. |
| 5,373,083 A | 12/1994 | King et al. |
| 5,380,907 A | 1/1995 | Mizukami et al. |
| 5,498,789 A | 3/1996 | Takagi et al. |
| 5,502,232 A | 3/1996 | Buysch et al. |
| 5,543,547 A | 8/1996 | Iwane et al. |
| 5,726,340 A | 3/1998 | Takagi et al. |
| 5,760,272 A | 6/1998 | Pressman et al. |
| 5,821,377 A | 10/1998 | Buysch et al. |
| 5,856,554 A | 1/1999 | Buysch et al. |
| 6,114,564 A | 9/2000 | Pressman et al. |
| 6,172,254 B1 | 1/2001 | Pressman et al. |
| 6,180,812 B1 | 1/2001 | Johnson et al. |
| 6,197,991 B1 | 3/2001 | Spivack et al. |
| 6,346,499 B1 | 2/2002 | Johnson et al. |
| 6,346,500 B1 | 2/2002 | Pressman et al. |

FOREIGN PATENT DOCUMENTS

| | | |
|---|---|---|
| DE | 736325 | 3/1996 |
| EP | 0071286 | 2/1983 |
| JP | 10158221 | 6/1980 |
| JP | 94-271506 | 9/1994 |
| JP | 94-271509 | 9/1994 |
| JP | 95-145107 | 6/1995 |
| JP | 96-89810 | 4/1996 |
| JP | 96-92168 | 4/1996 |
| JP | 96-193056 | 7/1996 |
| JP | 97-110804 | 4/1997 |
| JP | 97-255629 | 9/1997 |
| JP | 97-278715 | * 10/1997 |
| JP | 97-278716 | 10/1997 |
| JP | 10316627 | 12/1998 |
| WO | WO 00/37413 | 6/2000 |
| WO | WO 00/37419 | 6/2000 |

* cited by examiner

*Primary Examiner*—Robert D. Harlan
(74) *Attorney, Agent, or Firm*—Andrew J. Caruso; William E. Powell, III

(57) ABSTRACT

The present disclosure is directed to a catalyst composition used in the production of aromatic carbonates, and in particular to a catalyst composition which comprises an activating solvent. In one embodiment the disclosure relates to a catalyst composition which comprises to a combination of two activating solvents, a first activating solvent chosen for its coordinative properties, and a second activating solvent chosen for its dielectric constant properties. In alternative embodiments, the present disclosure also pertains to a method for producing aromatic carbonates using the catalyst compositions disclosed herein.

9 Claims, No Drawings

METHOD AND CATALYST COMPOSITION FOR PRODUCING AROMATIC CARBONATES USING ACTIVATING SOLVENTS

BACKGROUND OF INVENTION

The present disclosure is directed to a catalyst composition used in the production of aromatic carbonates, and in particular to a catalyst composition which comprises an activating solvent. In one embodiment, the catalyst composition comprises combination of at least two activating solvents, a first activating solvent chosen for its coordinative properties, and a second activating solvent chosen for its dielectric constant properties. In other embodiments, the present disclosure also pertains to methods for producing aromatic carbonates using the catalyst compositions disclosed herein.

A useful method for the production of aromatic carbonates includes the oxidative carbonylation of aromatic hydroxy compounds, with carbon monoxide and oxygen, which is typically catalyzed by a catalyst composition comprising a Group 8, 9 or 10 metal catalyst, a salt source, optionally various metal co-catalyst sources, and optionally a base source. In some instances, a significant improvement to catalyst performance, in terms of both of activity and selectivity, can be achieved when the catalyst composition further includes an activating solvent. The use of certain activating solvents are known to aid in the dissolution and dissociation of certain components of a carbonylation catalyst composition in a typical carbonylation reaction mixture. For instance, the solubility and dissociation of alkali halide and alkaline earth halide salt sources in typical carbonylation reaction mixtures comprising aromatic hydroxy compounds are known to be significantly improved when certain types of activating solvents are present in the catalyst composition.

SUMMARY OF INVENTION

In one embodiment, the present disclosure pertains to a carbonylation catalyst composition and method, which catalyzes the production of diaryl carbonates from aromatic hydroxy compounds, carbon monoxide and oxygen, said carbonylation catalyst composition comprising a combination of a first activating solvent and a second activating solvent.

In another embodiment, the present disclosure pertains to a carbonylation catalyst composition and method, which catalyzes the production of diaryl carbonates from aromatic hydroxy compounds, carbon monoxide and oxygen, said carbonylation catalyst composition comprising an activating solvent that is an alkyl carbonate.

In another embodiment, the present disclosure pertains to a carbonylation catalyst composition and method, which catalyzes the production of diaryl carbonates from aromatic hydroxy compounds, carbon monoxide and oxygen, said carbonylation catalyst composition comprising an activating solvent that is a nitroaromatic solvent.

DETAILED DESCRIPTION

The present disclosure relates to several embodiments of an invention, which pertains to a carbonylation catalyst composition used in the production of diaryl carbonates from aromatic hydroxy compounds, carbon monoxide, and oxygen, wherein the carbonylation catalyst composition comprises an activating solvent. In an alternative embodiment the catalyst composition comprises a combination of at least two activating solvents, a first activating solvent chosen for its coordinative properties, and a second activating solvent chosen for its dielectric constant properties.

In the context of the present invention, the terms "active" and "activated", when used in reference to the catalytic state of a complete catalyst composition, are meant to imply a condition in which the catalyst composition can catalyze the production of a desired aromatic carbonate at a rate which is greater than, or equal to, a predetermined reference rate. However, in the context of the present invention the term "activating solvent", when used in reference to a solvent component of a catalyst composition, is meant to imply that the solvent component serves a functional role in catalyzing the production of a desired aromatic carbonate, and is not present simply as a diluent. Herein, the rate of an oxidative carbonylation reaction is defined in terms of moles DPC formed in the presence of a catalyst per unit volume per hour (mol/L*hr). Herein, the catalyst productivity is defined in terms of "turnover number" (TON), which is a measure of moles of desired carbonate produced per mole of catalyst during reaction time. For example, in one embodiment of the present invention, the palladium catalyst Pd TON=[(moles of diphenyl carbonate)/(moles of palladium)]. In the context of the present invention, the term "de-activated", when used in reference to a catalyst composition, connotes a formerly "active" catalyst composition which in it's current state, produces a desired aromatic carbonate at a rate which is below a predetermined reference rate.

In the context of the present invention, the term "reaction condition" is meant to include, but is not limited to, reactor vessel pressure, reactor vessel temperature, reaction mixture temperature, agitation rate, gas flow rates (e.g., carbon monoxide flow rate and oxygen flow rate), gas mixture composition (e.g., the ratio of carbon monoxide to oxygen, or the presence of an additional gas source such as nitrogen), the pH of the reaction mixture, the weight % of various components of the liquid reaction mixture including, but not limited to, the weight % of an aromatic hydroxy compound, the weight % of a desired carbonate, and the weight % of water.

In the context of the present invention, the term "liquid reaction mixture" is defined as a mixture of compounds, which are present predominantly in a liquid state at a temperature of between about 25° C. and about 100° C., and a pressure of between about 0.1 MPa and about 10 MPa. Liquid reaction mixtures can be homogeneous liquid mixtures composed of one of more phases (e.g., biphasic liquid reaction mixtures), or heterogeneous liquid-solid mixtures containing components that are present in the solid state (e.g., precipitates). Herein, the individual constituents of a liquid reaction mixture are referred to as "components". The components of a typical first liquid reaction mixture include, but are not limited to, the desired aromatic carbonate, byproducts of the carbonylation reaction which include, but are not limited to, halogenated aromatic hydroxy compounds (e.g., 2-bromophenol, 4-bromophenol), water, aryl ethers, poly-aromatic hydroxy compounds, and aromatic carbonates other than the desired aromatic carbonate, dissolved reagent gases, soluble components of the catalyst composition including activating solvents, insoluble components of the catalyst composition which are present as precipitates, and unreacted aromatic hydroxy compound. Suitable types of aromatic hydroxy compounds include, but are not limited to, monocyclic aromatic compounds comprising at least one hydroxy group, and polycyclic aromatic compounds comprising at least one hydroxy group. Illustrative examples of suitable aromatic hydroxy compounds include, but are not limited to, phenol, alkylphenols, alkoxyphenols, bisphenols, biphenols, and salicylic acid derivates (e.g., methyl salicylate).

The carbonylation catalyst compositions disclosed herein typically comprise a Group 8, 9 or 10 metal source as a catalyst, a salt source, and a combination of at least two activating solvents. Optionally, at least one member selected from the group consisting of a first inorganic co-catalyst (IOCC), a second IOCC, a base source, and any mixtures thereof can be present in the catalyst composition. Suitable Group 8, 9 or 10 metal sources, which are also known as Platinum Group metal sources, include ruthenium sources, rhodium sources, palladium sources, osmium sources, iridium sources, and platinum sources. In one embodiment, about 1 ppm to about 10000 ppm of a Group 8, 9, or 10 metal source is present in the catalyst composition. In another embodiment, about 1 ppm to about 1000 ppm of a the Group 8, 9, or 10 metal source is present in the catalyst composition. In yet another embodiment of the present invention, about 1 ppm to about 100 ppm of a Group 8, 9, or 10 metal source is present in the catalyst composition. A typical Group 8, 9, or 10 metal source is a palladium source, including palladium compounds. As used herein, with respect to metal sources in general, the term "compound" includes inorganic, coordination and organometallic complex compounds. The compounds are typically neutral, cationic, or anionic, depending on the charges carried by the central metal and the coordinated ligands. Other common names for these compounds include complex ions (if electrically charged), Werner complexes, and coordination complexes. The Group 8, 9, or 10 metal source is typically present in the reaction mixture in a homogeneous form that is partially soluble in the reaction mixture, or alternatively in a heterogeneous form which is partially insoluble in the reaction mixture, including metal sources supported on substrates and polymer bound metal sources. Examples of suitable palladium sources include, but are not limited to, palladium sponge, palladium black, palladium deposited on carbon, palladium deposited on alumina, palladium deposited on silica, palladium halides, palladium nitrates, palladium carboxylates, palladium acetates, palladium salts of β-diketones, palladium salts of β-ketoesters, and palladium compounds containing at least one of the following ligands: carbon monoxide, amine, nitrite, nitrile, isonitrile, phosphine, phosphite, phosphate, alkoxide, alkyl, aryl, silyl or olefin.

Additional metal sources which are present in the catalyst compositions are typically referred to as inorganic co-catalysts. As used herein, the term "inorganic co-catalyst" (IOCC) includes any catalyst component that contains a metal element, which is present in the catalyst composition in addition to the Group 8, 9 or 10 first metal source. Typically, one or two IOCC's are present in the catalyst composition, and thus are present in the reaction mixture as a second metal source and a third metal source, respectively. In one embodiment, about 1 equivalent to about 1000 equivalents of at least one IOCC source, versus the amount of a Group 8, 9, or 10 metal source, is present in the catalyst composition. In another embodiment, about 1 equivalent to about 500 equivalents of at least one IOCC source, versus the amount of a Group 8, 9, or 10 metal source, is present in the catalyst composition. In yet another embodiment of the present invention, about 1 equivalent to about 100 equivalents of at least one IOCC source, versus the amount of a Group 8, 9, or 10 metal source, is present in the catalyst composition. In the present invention, typical IOCC's include, but are not limited to, compounds selected from the group consisting of Group 4 metal sources, Group 7 metal sources, Group 9 metal sources, Group 11 metal sources, Group 14 metal sources, and Lanthanide sources. Suitable examples of IOCC sources include, but are not limited to, titanium sources, manganese sources, cobalt sources, copper sources, lead sources, and cerium sources. Suitable forms of IOCC sources include, but are not limited to, elemental metals, metal oxides, and metal compounds in stable oxidation states, which can be neutral, cationic, or anionic, depending on the charges carried by the central atom and the coordinated ligands. For example, in one embodiment the first and second IOCC sources are initially present in the carbonylation catalyst composition as titanyl (IV)oxide-bis-2,4-pentanedionate, and copper(II)-bis-2,4-pentanedionate, respectively.

Typically, the carbonylation catalyst composition further comprises at least one salt source. Illustrative examples of suitable salt sources include, but are not limited to, alkali halides, alkaline-earth halides, guanidinium halides, and onium halides (e.g., ammonium halides, phosphonium halides, sulfonium halides), and compounds, which contain an anion, selected from the group consisting of carboxylates, acetates, and nitrates. Typical onium cations contain organic residues, which include C1–C20 alkyl, C6–C10 aryl, or alkyl-aryl combinations thereof. In one embodiment, about 1 equivalent to about 100000 equivalents of a salt source, versus the amount of a Group 8, 9, or 10 metal source, is present in the catalyst composition. In another embodiment, about 1 equivalent to about 10000 equivalents of a salt source, versus the amount of a Group 8, 9, or 10 metal source, is present in the catalyst composition. In yet another embodiment of the present invention, about 1 equivalent to about 1000 equivalents of a salt source, versus the amount of a Group 8, 9, or 10 metal source, is present in the catalyst composition.

In one embodiment, the catalyst composition further comprises a combination of at least two activating solvent. Typically, about 1 weight % to about 30 weight % of each activating solvent, based on the total weight of the liquid reaction mixture, is used. In another embodiment, about 1 weight % to about 20 weight % of each activating solvent, based on the total weight of the liquid reaction mixture, is used. In yet another embodiment of the present invention, about 1 weight % to about 10 weight % of each activating solvent, based on the total weight of the liquid reaction mixture, is used.

For the present invention, examples of a first activating solvent that possess suitable coordinative properties include, but are not limited to, polyether solvents (e.g., diglyme, triglyme, tetraglyme and crown ethers) C2–C8 aliphatic or C7–C10 aromatic mononitriles or dinitriles solvents (e.g., acetonitrile, adiponitrile, succinonitrile, adiponitrile, and benzodinitrile), sulfones, and any mixtures thereof. In the context of the present invention, the term "coordinative" is defined as a compound that contains at least one lone pair of electrons, and can function as a Lewis base.

In the context of the present disclosure the term "dielectric constant", which herein is represented by the symbol epsilon ($\epsilon$), is defined as a measure in the reduction of an electric field around a charged particle dissolved in a solvent, as compared to the electric field strength around the same particle in a vacuum. The dielectric constant of a medium, specifically a solvent, is a macroscopic property. The higher the dielectric constant of a given solvent is, the lower the electrostatic forces, both attractive and repulsive, are between two ions dissolved in the solvent. For example, ions of opposite charge have a higher tendency to dissociate in a solvent with a high dielectric constant. Generally, a solvent with a dielectric constant lower than about 10 ($\epsilon<10$) is considered to be a non-polar solvent in which ionic solutes are only sparingly soluble, and will be highly associated. Consequently, most solvents with a dielectric constant greater than or equal to about 10 are considered to be polar solvents in which ionic solutes are typically very soluble, and will are highly dissociated in solution.

In the context of the present invention, examples of a second activating solvent which possesses suitable dielectric constant characteristics (e.g. a dielectric constant greater than or equal to about 20) include, but are not limited to, protic solvents, formic acid, t-butyl acetic acid, foramide, and nitroaromatic compounds such as nitroanilines, as well as aprotic solvents such as acetone, thioacetone, N,N-dimethylformamide, acetonitrile, adiponitrile, nitromethane, nitrobenzene and its alkyl and halo derivatives, hexamethylphosphoramide, acetamides, propioamides, N-methylpyrolidone, sulfolane, sulfoxide, organic carbonates including cyclic carbonates and any mixtures thereof.

In another embodiment, the carbonylation catalyst composition further comprises at least one base source. Suitable types of base sources include, but are not limited to, basic oxides, hydroxides, mono-alkoxides, poly-alkoxides, monocyclic aryloxides, polycyclic aryloxides, and tertiary amines. Illustrative examples of suitable base sources include, but are not limited to, sodium hydroxide, lithium hydroxide, potassium hydroxide, tetraalkylammonium hydroxides (e.g. tetramethylammonium hydroxide, tetraethylammonium hydroxide, methyltributylammonium hydroxide, and tetrabutylammonium hydroxide) sodium phenoxide, lithium phenoxide, potassium phenoxide, tetraalkylammonium phenoxides (e.g. tetramethylammonium phenoxide, tetraethylammonium phenoxide, methyltributylammonium phenoxide, and tetrabutylammonium phenoxide), triethyl amine, and tributyl amine. In one embodiment, about 1 equivalent to about 10000 equivalents of a base source, versus the amount of a Group 8, 9, or 10 metal source, is present in the reaction mixture. In another embodiment, about 1 equivalent to about 1000 equivalents of a base source, versus the amount of a Group 8, 9, or 10 metal source, is present in the reaction mixture. In yet another embodiment of the present invention, about 1 equivalent to about 500 equivalents of a base source, versus the amount of a Group 8, 9, or 10 metal source, is present in the reaction mixture.

The following examples are included to provide additional guidance to those skilled in the art in practicing the claimed invention. The examples provided are merely representative of the present invention. Accordingly, the following examples are not intended to limit the invention, as defined in the appended claims, in any manner.

EXAMPLES

General Procedure for examples 1–10: Carbonylation reaction mixtures comprised phenol solutions (about 63.5 g) containing about 20 parts per million (ppm) palladium added as palladium(II) 2,4-pentanedionate (about 0.0043 g), lead added as lead(II) oxide (about 0.188 g), titanium added as titanium(IV) oxide 2,4-pentanedionate (about 0.08 g), sodium bromide (about 0.187 g), as well as the activating solvents listed in Tables 1 and 2 (tetraglyme (TG), acetonitrile (ACN), nitrobenzene (NBz), ethylene carbonate (EC), propylene carbonate (PC), dimethylacetamide (DMA), N-methylacetamide (NMA), sulfolane (SL)). Reactions were carried out using a constant composition gas-flow Hastelloy-C autoclave for about 2.5 hours at about 100° C. in a premixed gas mixture containing about 8.7 mol % oxygen in carbon monoxide at a total pressure of about 10.3 MPa. Molecular sieves (1/16" pellets, 3 Å, 30 g) were placed in a perforated Teflon basket mounted to the stir shaft of the reactor. Reaction mixtures were analyzed by gas chromatography (GC) after 2.5 hours of reaction.

Results are shown in Tables 1 and 2.

TABLE 1

| | Activating Solvent (wt %) | Diphenyl Carbonate (wt %) | Rate (mol/L hr) | Pd TON | Selectivity (%) |
|---|---|---|---|---|---|
| 1 (control) | — | 3.3 | 0.07 | 875 | 32 |
| 2 | NBz (14) | 6.1 | 0.14 | 1625 | 41 |
| 3 | EC (7) | 13.1 | 0.27 | 3053 | 67 |
| 4 | PC (7) | 9.1 | 0.20 | 2377 | 68 |

TABLE 2

| | First Activating Solvent (wt %) | Second Activating Solvent (wt %) | Diphenyl Carbonate (wt %) | Rate (mol/L hr) | Pd TON | Selectivity (%) |
|---|---|---|---|---|---|---|
| 5 (control) | TG (5) | — | 23.3 | 0.5 | 5760 | 94 |
| 6 (control) | ACN (13) | — | 19 | 0.43 | 5126 | 66 |
| 7 | TG (5) | ACN (13) | 25.8 | 0.53 | 7766 | 74 |
| 8 | TG (5) | NBz (13) | 27.3 | 0.52 | 7244 | 81 |
| 9 | TG (5) | EC (7) | 24.8 | 0.51 | 6621 | 92 |
| 10 | TG (5) | PC (7) | 26.6 | 0.52 | 6652 | 81 |
| 11 | TG (5) | DMA (12) | 24.0 | 0.46 | 6591 | 83 |
| 12* | TG (5) | NMA (13) | 19.6 | 0.39 | 7003 | 78 |
| 13 | TG (5) | SL (11) | 17.8 | 0.36 | 4929 | 94 |

*15 ppm Pd used

General Procedure fore examples 14–16: Carbonylation reaction mixtures comprised phenol solution (about 61.5 g) containing about 14 parts per million (ppm) palladium added as palladium(II) 2,4-pentanedionate (about 0.00265 g), copper added as copper(II) 2,4-pentanedionate (about 0.039 g), titanium added as titanium (IV) oxide 2,4-pentanedionate (about 0.078 g), sodium bromide (about 0.336 g), sodium hydroxide (about 0.205 g), as well as the activating solvents listed in table 2 (tetraglyme (TG), ethylene carbonate (EC)), dimethylacetamide (DMA)). Reactions were carried out using a constant composition gas-flow Hastelloy-C autoclave for about 2.5 hours at about 100° C. in a premixed gas mixture containing about 8.9 mol % oxygen in carbon monoxide at a total pressure of about 10.3 MPa. Molecular sieves (1/16" pellets, 3 Å, 30 g) were placed in a perforated Teflon basket mounted to the stir shaft of the reactor. Reaction mixtures were analyzed by gas chromatography (GC) after 2.5 hours of reaction. Results are shown in Table 3.

TABLE 3

| | First Activating Solvent (wt %) | Second Activating Solvent (wt %) | Diphenyl Carbonate (wt %) | Rate (mol/L hr) | Pd TON | Selectivity (%) |
|---|---|---|---|---|---|---|
| 14 (control) | TG (3.5) | — | 27.9 | 0.56 | 9836 | 76 |
| 15 | TG (7) | — | 31.9 | 0.66 | 11581 | 83 |

TABLE 3-continued

| | First Activating Solvent (wt %) | Second Activating Solvent (wt %) | Diphenyl Carbonate (wt %) | Rate (mol/ L hr) | Pd TON | Selectivity (%) |
|---|---|---|---|---|---|---|
| (control) 16 | TG (3.5) | EC (7) | 32.3 | 0.66 | 11926 | 81 |

While the invention has been illustrated and described, it is not intended to be limited to the details shown, since various modifications and substitutions can be made without departing in any way from the spirit of the present invention. As such, further modifications and equivalents of the invention herein disclosed can occur to persons skilled in the art using no more than routine experimentation, and all such modifications and equivalents are believed to be within the spirit and scope of the invention as defined by the following claims.

What is claimed is:

1. A method for carbonylating an aromatic hydroxy compound, comprising the step of contacting at least one aromatic hydroxy compound with oxygen and carbon monoxide in the presence of a carbonylation catalyst composition, said carbonylation catalyst composition comprising a combination of a first activating solvent and a second activating solvent.

2. The method of claim 1, wherein said first activating solvent is a solvent with coordinative properties, and said second activating solvent is a solvent with a dielectric constant greater than or equal to about 20.

3. The method of claim 1, wherein the first activating solvent is one member selected from the group consisting of a polyether solvent, a nitrile solvent, a dinitrile solvent, an amide solvent, and a sulfone solvent.

4. The method of claim 1, wherein the second activating solvent is one member selected from the group consisting of formic acid, t-butyl acetic acid, foramide, nitroanilines, acetone, thioacetone, N,N-dimethylformamide, acetonitrile, adiponitrile, nitromethane, nitrobenzene, hexamethylphosphoramide, acetamides, propioamides, N-methylpyrolidone, sulfolane, sulfoxides, ethylene carbonate, propylene carbonate, alkylcarbonates.

5. The method of claim 1, wherein the first activating solvent is tetraglyme, and the second activating solvent is one member selected from the group consisting of nitrobenzene, ethylene carbonate, and propylene carbonate.

6. The method of claim 1, further comprising a catalyst metal source selected from the group consisting of a Group 8 metal source, a Group 9 metal source, and a Group 10 metal source.

7. The method of claim 6, wherein the catalyst source is a palladium source.

8. A method for carbonylating an aromatic hydroxy compound, comprising the step of contacting at least one aromatic hydroxy compound with oxygen and carbon monoxide in the presence of a carbonylation catalyst composition, said carbonylation catalyst composition comprising an activating solvent that is an alkyl carbonate.

9. A method for carbonylating an aromatic hydroxy compound, comprising the step of contacting at least one aromatic hydroxy compound with oxygen and carbon monoxide in the presence of a carbonylation catalyst composition, said carbonylation catalyst composition comprising an activating solvent that is a nitroaromatic solvent.

* * * * *